(12) United States Patent
Mutin et al.

(10) Patent No.: US 8,586,758 B2
(45) Date of Patent: Nov. 19, 2013

(54) PREPARATION OF AN INORGANIC SUBSTRATE HAVING ANTIMICROBIAL PROPERTIES

(75) Inventors: Hubert Mutin, Clapiers (FR); Gilles Guerrero, Béziers (FR); Julien Almaric, Laroques des Albères (FR)

(73) Assignees: Centre National de la Recherche Scientifique, Paris (FR); Universite Montpellier II Sciences et Techniques du Languedoc, Montpellier (FR)

( * ) Notice: Subject to any disclaimer, the term of this patent is extended or adjusted under 35 U.S.C. 154(b) by 760 days.

(21) Appl. No.: 12/160,882

(22) PCT Filed: Dec. 21, 2006

(86) PCT No.: PCT/FR2006/002828
§ 371 (c)(1),
(2), (4) Date: May 17, 2010

(87) PCT Pub. No.: WO2007/080291
PCT Pub. Date: Jul. 19, 2007

(65) Prior Publication Data
US 2010/0249425 A1    Sep. 30, 2010

(30) Foreign Application Priority Data

Jan. 13, 2006 (FR) ...................................... 06 00291

(51) Int. Cl.
*C07F 9/38*      (2006.01)
(52) U.S. Cl.
USPC ......................................................... 548/112
(58) Field of Classification Search
USPC ......................................................... 548/112
See application file for complete search history.

(56) References Cited

U.S. PATENT DOCUMENTS

| 4,962,073 A | 10/1990 | Martin | |
|---|---|---|---|
| 2002/0009604 A1 * | 1/2002 | Zamora et al. | 428/450 |

FOREIGN PATENT DOCUMENTS

| DE | 102 11 562 | | 10/2003 | |
| EP | 1 157 994 | | 11/2001 | |
| EP | 1 180 396 | | 2/2002 | |
| EP | 1 180 396 A1 | * | 2/2002 | ............... B01J 20/32 |
| EP | 1 493 452 | | 6/2004 | |
| EP | 1 488 815 | | 12/2004 | |
| WO | WO 0112740 | * | 2/2001 | ............... C09G 1/02 |
| WO | WO 03/039602 | | 5/2003 | |
| WO | WO 03/041754 | | 5/2003 | |
| WO | WO 03/099346 | | 12/2003 | |

OTHER PUBLICATIONS

Moncada et al. International union of pharmacology nomenclature in nitric oxide research. Pharmacol Rev 49:137-142, 1997.*
Russell et al. The reaction of nitrogen(II) oxide with various primary and secondary amines. J Am Chem Soc 83, 1819-1822, Apr. 1961.*
International Search Report dated Jun. 13, 2007.

* cited by examiner

*Primary Examiner* — Wu-Cheng Winston Shen
*Assistant Examiner* — Yih-Horng Shiao
(74) *Attorney, Agent, or Firm* — Merchant & Gould

(57) ABSTRACT

The invention relates to a process for modifying an inorganic substrate, directed toward giving it antimicrobial properties, said process consisting in grafting in one or more steps onto a surface of said substrate groups with intrinsic antimicrobial properties or groups capable of releasing species with antimicrobial properties. The grafting is performed by means of an organophosphorus coupling agent.
A subject of the invention is similarly a substrate obtained by this process, as well as diverse uses of such a substrate.

7 Claims, No Drawings

PREPARATION OF AN INORGANIC SUBSTRATE HAVING ANTIMICROBIAL PROPERTIES

The present invention relates to a process for preparing an inorganic substrate with antimicrobial properties, and also to a substrate obtained by this process and to the use of such a substrate.

BACKGROUND OF THE INVENTION

Microorganisms such as bacteria are capable of growing by combining on the surface of inorganic substrates, forming a biofilm. This mode of growth is directly involved in a large number of bacterial infections, which may arise, for example, in the food industry sector, via pipework, or in the medical sector, during the insertion of prostheses or implants.

To prevent the formation of biofilms, it is known practice to modify the surface of inorganic substrates by grafting molecules with antimicrobial properties, or molecules that release groups with antimicrobial properties. Organosilicon coupling agents have been used to this effect for many years.

However, organosilicon agents cannot be used for all types of substrates. For example, they are unsuitable for substrates of phosphate or calcium carbonate type. In addition, the process for forming such coatings is complicated due to the fact that these organosilicon agents are moisture-sensitive. Furthermore, the coatings obtained with these coupling agents are moisture-sensitive, in particular in basic medium.

To overcome these drawbacks, the inventors have found that it is possible to use organophosphorus coupling agents to bind to various substrates groups with antimicrobial properties or capable of releasing a component that has antimicrobial properties.

This solution has many advantages over the prior-art techniques.

Firstly, it is possible to treat with the same coupling agents a very wide variety of substrates (metals and metal alloys, metal oxides, metal hydroxides, and metal carbonates and phosphates). This makes it possible especially to satisfy the needs in the medical sector, in which no satisfactory general solution had hitherto been found for reducing the risks of infection following the insertion of prostheses or implants, in particular on account of the very wide diversity of materials used. In addition, it is thus possible to treat a complex object constituted by different materials, or to treat objects of the same family each constituted by a single material which may vary from one object to another.

Moreover, the grafting process may be performed under easier conditions than those of the prior art, for example in ambient air, under non-anhydrous conditions, or even in water, which makes it possible to avoid the use of organic solvents.

It is also possible to prepare surface coatings that are very stable in the presence of water, and even at basic pH, allowing sterilization by wet autoclaving or washing with a basic disinfectant such as bleach.

The search for and development of a solution for the production of coatings for objects intended to be used in the medical sector may be transposed to the production of industrial objects, such as taps or valves constituted of several materials, or of objects constituted of materials that may vary, such as steel, zinc steel or copper pipes, these objects being intended, for example, to be used in cooling towers or hot water distribution circuits. The possibility of working in water makes it possible to envision a treatment by simple circulation, in an existing installation, of a dilute solution of the coupling agent in water.

SUMMARY OF THE INVENTION

Thus, according to a first aspect, the invention relates to a process for modifying an inorganic substrate, directed toward giving it antimicrobial properties. Said process consists in grafting in one or more steps onto a surface of said substrate groups with intrinsic antimicrobial properties or groups capable of releasing species with antimicrobial properties, and it is characterized in that the grafting is performed by means of an organophosphorus coupling agent chosen from the phosphonic acids and phosphonates of formula (I) $RPO(OX)_2$, the bis-phosphonates of formula (II) $RR'[PO(OX)_2]_2$, the phosphinic acids and phosphinates of formula (III) $RR'PO(OX)$, the monoalkyl phosphates of formula (IV) $ROPO(OX)_2$, and the dialkyl phosphates of formula (V) $(RO)(R'O)PO(OX)$, in which:

X represents a hydrogen atom or a group chosen from metal ions, ammonium ions, alkyl or aryl groups containing from 1 to 6 carbon atoms and trialkylsilyl groups containing from 1 to 6 carbon atoms;

R is an organic group chosen from:
  groups with intrinsic antimicrobial properties;
  groups that are capable of releasing species with antimicrobial properties, chosen from groups that release nitrogen monoxide and groups that release carboxylic acids;
  groups R" which, after modification, have intrinsic antimicrobial properties or are capable of releasing species with antimicrobial properties, said groups R" being chosen from the groups $-(CH_2)_n-SH$, $-(CH_2)_n-CN$, $-(CH_2)_n-NH_2$, $-(CH_2)_n-[NH-(CH_2)_{n'}]_{n''}-NH_2$, $-(CH_2)_n-NMe_2$, $-(CH_2)_n-Hal$, Hal representing a halogen atom such as Br, Cl or I, and in which n is between 1 and 20, n' is between 1 and 5 and n" is between 1 and 10;

R' is a hydrogen atom, a hydroxyl group or an organic group corresponding to the definition given for the groups R above.

Among the groups with intrinsic antimicrobial properties, mention may be made of groups comprising one or more ammonium, pyridinium, imidazolium, phosphonium, sulfate, biguanide, carbanilide, amidine, pyrimidine, hydroxyquinoline or carboxylic acid groups, peptides or enzymes.

According to one embodiment, the coupling agent is diethyl 3-(N-methylimidazolium bromide)propylphosphonate (MImBPPE). In this case, the compound corresponds to formula (I) in which R=BrMeIm—$(CH_2)_3$—, and X is an ethyl group.

According to another embodiment, the coupling agent is 3-(N-methylimidazolium bromide)propylphosphonic acid (MImBPPA). In this case, the compound corresponds to formula (I) in which R=BrMeIm—$(CH_2)_3$—, and X is a hydrogen atom.

Among the groups that are capable of releasing nitrogen monoxide, mention may be made of diazenium diolate or oxynitroxy groups, and among the groups capable of releasing carboxylic acids, mention may be made of ester or amide groups.

When R is of the type R", the process includes one or more additional steps.

For example, if R" is $-(CH_2)_n-SH$, $-(CH_2)_n-CN$, $-(CH_2)_n-NB_2$ or any other complexing group, the modification may be performed by immersion in a solution of silver nanoparticles or in a solution of $AgNO_3$, so as to allow the release of $Ag^+$ ions in physiological medium.

If R" is $-(CH_2)_n-NH_2$, or $-(CH_2)_n-NH-(CH_2)_2-NH_2$, the modification may be performed by working under an atmosphere of nitrogen monoxide gas, so as to allow the release of nitrogen monoxide in physiological medium.

If R" is $-(CH_2)_n-NMe_2$, the modification may be performed by heating in a solution of alkyl bromide, so as to allow the formation of quaternary ammonium functions with intrinsic antimicrobial properties.

If R" is $-(CH_2)_n-Hal$ with Hal=Cl, Br or I, the modification may be performed by heating in a solution of triethylamine, so as to allow the formation of quaternary ammonium functions.

DETAILED DESCRIPTION OF THE PREFERRED EMBODIMENTS

According to one embodiment, the coupling agent is 12-mercaptododecylphosphonic acid (MDPA). This compound corresponds to formula (I) in which $R=R''=-(CH_2)_{12}-SH$, and X is a hydrogen atom.

According to another embodiment, the coupling agent is 2-aminoethylphosphonic acid (AEPA). This compound corresponds to formula (I) in which $R=R''=-(CH_2)_2-NH_2$, and X is a hydrogen atom.

According to another embodiment, the coupling agent is diethyl 3-aminopropylphosphonate (APPE). This compound corresponds to formula (I) in which $R=R''=-(CH_2)_3-NH_2$, and X is an ethyl group.

According to another embodiment, the coupling agent is 12-bromododecylphosphonic acid (BDPA). This compound corresponds to formula (I) in which $R=R''=-(CH_2)_{12}-Br$, and X is a hydrogen atom.

According to another embodiment, the coupling agent is diethyl 12-N-(aminoethyl)aminododecylphosphonate (AE-ADPE). This compound corresponds to formula (I) in which $R=R''=-(CH_2)_{12}-NH-(CH_2)_2-NH_2$, and X is an ethyl group.

According to another embodiment, the coupling agent is diethyl 3-(N,N-dimethylamino)dodecylphosphonate (DMADPE). This compound corresponds to formula (I) in which $R=R''=-(CH_2)_{12}-N(Me)_2$, and X is an ethyl group.

The substrate to be treated may be chosen from metals (for example stainless steel, a galvanized steel, titanium, hydroxyapatite-coated titanium, an alloy based on titanium or chromium, aluminum or copper), a metal oxide (for example titanium oxide, zirconium oxide or aluminum oxide), a metal hydroxide, a metal carbonate (for example a calcium carbonate) or a metal phosphate (for example hydroxyapatite). It may be in bulk form (plate, sheet, machined or molded component, metallic or ceramic) or in powder form, for example a $TiO_2$, $ZrO_2$, hydroxyapatite or calcium carbonate powder. When the substrate is in powder form, it may be advantageously used, once modified by the process according to the invention, as filler in organic polymers or for inclusion in the manufacture of coatings.

The coupling agent is grafted onto the surface of said substrate preferably by immersing said substrate in a solution containing said coupling agent.

The solvent used for the coupling agent may be water, alcohol, a water-alcohol mixture, or an organic solvent, for example toluene, dichloromethane, chloroform, DMSO, DMF or THF.

The concentration of coupling agent is generally between 0.1 and 100 mM. When the substrate is in plate form (very low specific surface area), the concentration of coupling agent is preferably between 0.1 and 10 mM, for example 0.5 or 1 mM. When the substrate is in powder form, the concentration of the coupling agent is preferably between 5 and 80 mM, as a function of the specific surface area.

The pH of the solution containing the coupling agent is chosen as a function of the substrate used, so as to avoid any dissolution of substrate.

According to a second aspect, a subject of the invention is a modified inorganic substrate obtained via the process according to the invention. Said substrate has a surface onto which are attached organophosphorus groups containing at least one organic substituent $R^1$, said organic substituent $R^1$ having antimicrobial properties or being capable of releasing, in physiological medium, a species with antimicrobial properties.

The organophosphorus groups are attached to the surface of the substrate via M—O—P bonds in which M represents the metal of the substrate. These bonds M—O—P originate from the condensation of the groups P=OX and/or from the coordination of the phosphoryl groups PE=O.

The organophosphorus groups are of phosphonate type of formula $R^1PO_{1-x}(OX)_{2-y}(OM)_{x+y}$, of bis-phosphonate type of formula $R^1R^2[PO_{1-x}(OX)_{2-y}(OM)_{x+y}]_2$, of phosphinate type of formula $R^1R^2PO_{1-x}(OX)_{1-z}(OM)_{x+z}$, of phosphate type of formula $R^1OPO_{1-x}(OX)_{2-y}(OM)_{x+y}$, or of diester type $(R^1O)(R^2O)PO\ R^1R^2PO_{1-x}(OX)_{1-z}(OM)_{x+z}$, in which:

X represents a hydrogen atom or a group chosen from metal ions, ammonium ions, alkyl or aryl groups containing from 1 to 6 carbon atoms and trialkylsilyl groups containing from 1 to 6 carbon atoms;

$R^1$ is an organic group chosen from:
groups with intrinsic antimicrobial properties;
groups capable of releasing species with antimicrobial properties, said groups being chosen from groups that release metal ions, groups that release nitrogen monoxide or groups that release carboxylic acids;

$R^2$ is a hydrogen atom, a hydroxyl group or an organic group that may optionally form part of the groups $R^1$ defined above;

M represents the metal of the substrate;
x is 0 or 1;
y is 0, 1, or 2;
z is 0 or 1.

The substrate may be a metal, a metal oxide, a metal hydroxide, a metal carbonate or a metal phosphate, bearing on its surface groups with antimicrobial properties or groups capable of releasing components with antimicrobial properties chosen from groups that release metal ions, groups that release nitrogen monoxide or groups that release carboxylic acids, these groups being attached by means of an organophosphorus group as defined above.

Among the groups that have intrinsic antimicrobial properties, mention may be made of groups comprising one or more ammonium, pyridinium, imidazolium, phosphonium, sulfate, biguanide, carbanilide, amidine, pyrimidine, hydroxyquinoline or carboxylic acid functions, peptides or enzymes.

Among the groups that release metal ions (silver, gold, copper or zinc), mention may be made of groups bearing one or more amine, acid, thiol, cyano or disulfide functions, complexing ions or metal particles. Among the groups that release nitrogen monoxide, mention may be made of diazenium diolate or oxynitroxy groups, and among the groups that release carboxylic acids, mention may be made of ester or amide groups.

In the substrate according to the invention, the group $R^1$ may be a group $-(CH_2)_{12}-SH$ that has bound $Ag^+$ ions, a group $-(CH_2)_{12}-SH$ that has bound silver particles, a group —$(CH_2)_{12}$—Br that has bound a tertiary amine to form a quaternary ammonium, a group —$(CH_2)_2$—$NMe_2$ that has bound alkyl bromide to form a quaternary ammonium, a group —$(CH_2)_2$—$NH_2$ that has bound nitrogen monoxide to form a diazenium diolate group, a group —$(CH_2)_3$—$NH_2$ that has bound nitrogen monoxide, a group —$(CH_2)_{12}$—NH—$(CH_2)_2$—$NH_2$ that has bound nitrogen monoxide, or a group —$(CH_2)_3$—$C_3H_3N_2MeBr$.

According to one embodiment, the modified substrate is constituted of a titanium sheet modified with MDPA and $Ag^+$ ions.

According to another embodiment, the modified substrate is constituted of a titanium sheet modified with MDPA and silver particles.

According to another embodiment, the modified substrate is constituted of a stainless steel sheet modified with MDPA and $Ag^+$ ions.

According to another embodiment, the modified substrate is constituted of a titanium sheet modified with AEPA and nitrogen monoxide NO.

According to another embodiment, the modified substrate is constituted of a sheet of stainless steel modified with AEPA and nitrogen monoxide NO.

According to another embodiment, the modified substrate is constituted of a titanium sheet modified with APPE and nitrogen monoxide NO.

According to another embodiment, the modified substrate is constituted of a sheet of stainless steel modified with APPE and nitrogen monoxide NO.

According to another embodiment, the modified substrate is constituted of a titanium sheet modified with MImBPPE.

According to another embodiment, the modified substrate is constituted of a sheet of stainless steel modified with MImBPPE.

According to another embodiment, the modified substrate is constituted of a $TiO_2$ powder modified with MImBPPE.

According to another embodiment, the modified substrate is constituted of a sheet of stainless steel modified with MImBPPA.

According to another embodiment, the modified substrate is constituted of a titanium sheet modified with AEADPE and nitrogen monoxide NO.

According to another embodiment, the modified substrate is constituted of a sheet of stainless steel modified with BDPA and triethylamine $Et_3N$.

According to another embodiment, the modified substrate is constituted of a $TiO_2$ powder modified with BDPA and then with triethylamine.

According to another embodiment, the modified substrate is constituted of a $TiO_2$ powder modified with DMADPE and then with ethyl bromide.

According to another embodiment, the modified substrate is constituted of a hydroxyapatite powder modified with MImBPPE.

According to another embodiment, the modified substrate is constituted of a calcium carbonate powder modified with MImBPPE.

According to another embodiment, the modified substrate is constituted of a hydroxyapatite powder modified with BDPA and then with triethylamine.

According to another embodiment, the modified substrate is constituted of a calcium carbonate powder modified with BDPA and then with triethylamine.

The invention also relates to the use of a substrate according to the invention in components such as metal or ceramic implants, surgical instruments, heat exchangers, pipework components, or articles formed from polymer-filler composite materials, in which the filler is modified via the process according to the invention.

The present invention is illustrated below by concrete implementation examples, to which it is not, however, limited.

Example 1

Preparation of a Titanium Sheet Modified with MDPA and Silver Nanoparticles

Preparation of MDPA

MDPA was synthesized in three steps. In the first step, diethyl 12-bromododecylphosphonate is prepared by reacting 1-12-dibromododecane (40 g, 120.6 mmol) with triethyl phosphite (26 ml, 150 mmol) at 150° C. for 12 hours under argon. After cooling, 100 ml of distilled water are added. The organic phase is extracted, washed with 50 ml of distilled water, dried over sodium sulfate, filtered and concentrated under reduced pressure. The product obtained, a pale yellow oil, is purified by chromatography on a column of silica gel (eluent: hexane/8% EtOAc) to give 20 g (43% yield) of diethyl 12-bromododecylphosphonate.

In the second step, diethyl 12-bromododecylphosphonate (20.01 g; 51.9 mmol) is reacted, under an inert atmosphere, with thiourea (4 g; 51.9 mmol) in 200 ml of water at 100° C. with stirring for 12 hours. After cooling, a solution of sodium hydroxide (2.07 g; 51.9 mmol) in 100 ml of water is added dropwise and the reaction mixture is refluxed for 3 hours. After cooling to room temperature, hydrochloric acid solution (32%) is added dropwise to pH 1. The solution is then stirred for 24 hours. The organic phase is then recovered with 100 ml of $CH_2Cl_2$, washed with distilled water, dried over sodium sulfate, filtered and evaporated under reduced pressure. The yellow oil obtained is purified by chromatography on a column of silica gel (eluent: hexane/8% EtOAc) to give 10.8 g (n=38.16 mmol) of diethyl 12-mercaptododecylphosphonate (52% yield).

In the third step, 2.4 g (6.2 mmol) of diethyl mercaptododecylphosphonate in 50 ml of dry $CH_2Cl_2$ are reacted, under an inert atmosphere, with 2.4 ml (18 mmol) of bromotrimethylsilane with stirring for 3 hours at room temperature. The solution obtained is then concentrated under reduced pressure, followed by addition of 50 ml of $CH_2Cl_2$ and 1.7 ml of distilled water. After stirring for 12 hours at room temperature, evaporating off the solvent and recrystallizing from a $CH_2Cl_2$/hexane mixture, 1.8 g of MDPA are obtained (90% yield).

Characterization of MDPA $^1$H NMR (250 MHz, $D_2O$, ppm): 1.30-1.67 (m, 22H, $(CH_2)_{11}CH_2SH$)), 2.55 (q, 2H, $CH_2SH$)

$^{13}$C NMR (100 MHz, $CDCl_3$, ppm): 21.7 (d, 8 Hz, $CH_2CH_2CH_2P$), 23.3 (d, 5 Hz, $CH_2CH_2P$), 24.7 (s, $CH_2SH$), 28.1 (s, $CH_2CH_2CH_2SH$), 28.1 (d, 5 Hz, $CH_2$—$(CH_2)_3$—P), 28.5 (s, $CH_2$—$(CH_2)_3SH$), 29 ($CH_2$—$(CH_2)_4SH$), 29.1 (s, $CH_2$—$(CH_2)_4P$), 29.2 (s, $CH_2$—$(CH_2)_5$—P), 29.1 (s, $CH_2$—$(CH_2)_6$—P), 33.2 (d, 14 Hz, $CH_2$—P) 33.9 (s, 2H, $CH_2CH_2SH$).

$^{31}$P NMR (101 MHz, $CDCl_3$, ppm) 31.2.

Preparation of a Solution of Silver Nanoparticles

A solution of silver nanoparticles is prepared by dissolving 0.5 g of silver nitrate in 40 g of deionized water containing 0.1% by weight of Tween 80. 10 g of a 0.05% solution of hydrazine monohydrate in deionized water are added dropwise. The mixture is then made up to 100 g with deionized water. The mixture is stirred at room temperature for 6 hours, and the suspension is then centrifuged in order to remove the coarser particles.

Preparation of the Modified Titanium Sheet

A titanium sheet (supplied by Aldrich), of 99.7% purity and 0.127 mm thick, and of dimensions 1.8 cm×1.8 cm, is cleaned by ultrasound in pentane for 4 minutes and then treated with UV-ozone for 30 minutes.

The sheet is then immersed in 5 ml of a solution of MDPA in absolute ethanol, at a concentration of 1 mM, for 24 hours at 25° C.

After reaction, the sheet is washed thoroughly with the reaction solvent and then rinsed successively with ethanol, water and chloroform.

The titanium sheet modified with MDPA is immersed for 15 hours in 5 ml of the solution of silver nanoparticles, and is then rinsed successively with ethanol, with water and with chloroform. An analysis by photoelectron spectroscopy confirms the presence of silver on the surface of the sample.

Example 2

Preparation of a Titanium Sheet Modified with MDPA and $Ag^+$ Ions

Preparation of MDPA

MDPA is prepared according to the procedure described in Example 1.

Preparation of the Modified Titanium Sheet

A titanium sheet (supplied by Aldrich, of purity 99.7%, 0.127 mm thick, and of dimensions 1 cm×1 cm) is modified with MDPA under the same operating conditions as for Example 1.

This sheet is then immersed for 2 hours in 5 ml of an $AgNO_3$ solution of concentration 1 mM in deionized water, and is then rinsed successively with ethanol, with water and with chloroform.

Example 3

Preparation of a Titanium Sheet Modified with AEPA and Nitrogen Monoxide

Preparation of the Modified Titanium Sheet

A titanium sheet is modified with AEPA (sold by the company Aldrich) under the same operating conditions as for Example 2, by replacing the MDPA solution with an aqueous AEPA solution of concentration 1 mM.

This sheet is placed for 3 days at 25° C. in a reactor under 5 bar of NO. The reactor is then flushed with dry argon.

Example 4

Preparation of a Titanium Sheet Modified with APPE and Nitrogen Monoxide

Preparation of the Compound APPE

The compound APPE is synthesized in two steps.

In the first step, the reaction of 3-bromopropyl-phthalimide with triethyl phosphite gives diethyl phthalimidopropylphosphonate. To this end, 24.22 g of bromopropylphthalimide are placed in a 250 ml round-bottomed flask containing 10 g of triethyl phosphite. The mixture is maintained at 140° C. for 12 hours under an argon atmosphere. The mixture is then degassed under reduced pressure.

The product is purified by chromatography on a column of silica with dichloromethane as eluent and then with a gradient of methanol (5% and then 10%). 17.33 g of diethyl phthalimidopropylphosphonate are recovered in a yield of 59%.

Characterization of the Diethyl Phthalimidopropylphosphonate

Rf: 0.20 ($CH_2Cl_2$)

$^1H$ NMR (250 MHz, $CDCl_3$, ppm): 1.33 (m, 6H, $CH_3CH_2O$), 1.74-2.03 (m, 4H, P—$CH_2$—$CH_2CH_2$—N), 3.78 (t, 2H, P—$CH_2$—$CH_2CH_2$—$NH_2$), 4.08 (m, 4H, $CH_3CH_2O$), 7.7-7.9 (m, 4H, aromatic ring)

$^{13}C$ NMR (100 MHz, $CDCl_3$, ppm): 16.11-16.5 (m, P—$OCH_2CH_3$, N—$CH_2$—$CH_2$—$CH_2$—P), 22.68 (t, broad, N—$CH_2$—$CH_2$—$CH_2$—P), 38.34 (d, N—$CH_2$—$CH_2$—$CH_2$—P), 61.45 (q, P—$OCH_2CH_3$), 123.29 (t, CHAr—CHAr=CAr), 132.05 (d, CHAr—CHAr=CAr), 134.05 (s, CAr—C(O)—N), 168.26 (s, CAr—C(O)—N).

$^{31}P$ NMR (101 MHz, $CDCl_3$, ppm): 31.24

Mass spectrometry (FAB+/GT) m/z: 326 (M+1)

In the second step, diethyl phthalimidopropyl-phosphonate is reacted with hydrazine monohydrate to give the compound APPE.

To this end, 23.08 g (46.1 mmol) of hydrazine monohydrate are added dropwise to 15 g (46.1 mmol) of diethyl phthalimidopropylphosphonate in about 500 ml of absolute ethanol. The reaction medium is stirred for 12 hours. The salts formed are filtered off and washed with ethanol. After evaporating off the ethanol, salts are again formed. These salts are washed with $CH_2Cl_2$ and filtered on a Millipore membrane (0.45 μm). The filtrate is recovered and the $CH_2Cl_2$ is evaporated off. A yellow oil is obtained. The crude product is purified by chromatography on a column of silica gel with a 90/10 $CHCl_3$/MeOH mixture as eluent. 4.6 g of diethyl 3-aminopropylphosphonate (APPE) are obtained in a yield of 51.8%.

Characterization of the Compound APPE $^1H$ NMR (250 MHz, $CDCl_3$, ppm): 1.33 (m, 6H, $CH_3CH_2O$), 1.64-1.87 (m, 4H, P—$CH_2$—$CH_2CH_2$—N), 2.77 (t, 2H, P—$CH_2$—$CH_2CH_2$—$NH_2$), 4.1 (m, 4H, $CH_3CH_2O$)

$^{31}P$ NMR (101 MHz, $CDCl_3$, ppm): 33.344

Preparation of the Modified Titanium Sheet

A titanium sheet is modified with APPE under the same operating conditions as for Example 1, by replacing the MDPA solution with a solution of APPE in chloroform of concentration 1 mM, and with heating for 5 days at 65° C.

This sheet is then placed for 3 days at 25° C. in a reactor under 5 bar of NO. The reactor is then flushed with dry argon.

Example 5

Preparation of a Titanium Sheet Modified with MImBPPE

Preparation of $Br^-Me$—$C_3H_3N_2^+$—$(CH_2)_3$—$PO_3Et_2$ (MImBPPE)

This compound is obtained in two steps. In the first step, diethyl 3-bromopropylphosphonate is prepared by reacting, under an inert atmosphere, 1-3-dibromopropane (90.9 g; 0.45 mol) with triethyl phosphite (49.8 g; 0.3 mol) at 140° C. for 12 hours, followed by distillation under reduced pressure (52% yield).

In the second step, MImBPPE is obtained by reacting diethyl 3-bromopropylphosphonate with 1-methylimidazole, according to the following procedure. 3.18 g (38.6 mmol) of 1-methylimidazole and 10.01 g (38.6 mmol) of diethyl 3-bromopropylphosphonate are added to a three-necked flask under argon containing 50 ml of dry THF. The reaction medium is maintained at 70° C. for 12 hours to give a two-phase mixture. After separation of the phases by settling, the resulting oily liquid is washed with 2×50 ml of THF. The orange oil obtained is washed again with 3×30 ml of anhydrous ether to give the expected product in the form of a brown oil in a yield of 60%.

Characterization of MImBPPE $^1$H NMR (δ, ppm, 200 MHz, $D_2O$): 1.22 (t, 6H, O—$CH_2$—$CH_3$), 2.17-1.77 (m, 4H, $CH_2$—$CH_2$—P), 3.80 (s, 3H, $CH_3$—N), 4.04 (m, 4H, O—$CH_2$—$CH_3$), 4.23 (t, 2H, $CH_2$—N), 7.36 (d, 1H, N—CH), 7.41 (d, 1H, N—CH), 8.67 (s, 1H, N—CH—N).

$^{31}$P NMR (δ, ppm, 81 MHz, $D_2O$): 31.01.

$^{13}$C NMR (δ ppm, 100 MHz, $D_2O$): 17.4 (O—$CH_2$—$CH_3$), 21.7 ppm ($CH_2$—$CH_2$—P), 23.1-24.3 (d, $CH_2$—P), 37.1 ($CH_3$—N), 50.2 (d, $CH_2$—N), 62.9 (d, $CH_2$—O), 123.4-124.8 (d, N—CH—CH—N), 137.7 (N—CH—N).

Preparation of a Titanium Sheet Modified with $Br^-Me$—$C_3H_3N_2^+$—$(CH_2)_3$—$PO_3Et_2$ (MImBPPE)

A titanium sheet is modified with MImBPPE under the same operating conditions as for Example 4, replacing the APPE solution with a solution of MImBPPE of concentration 1 mM in chloroform.

Example 6

Preparation of a Titanium Sheet Modified with AEADPE and Nitrogen Monoxide

Preparation of the Compound AEADPE

The compound AEADPE is synthesized in two steps.

In the first step, diethyl 12-bromododecylphosphonate is prepared according to the procedure described in Example 1.

In the second step, diethyl 12-bromododecylphosphonate (3.85 g; 10 mmol) is added dropwise with stirring to ethylenediamine (4.01 g; 100 mmol) at room temperature. After stirring for two hours at room temperature, 100 ml of ethyl acetate are added and a two-phase medium is obtained. The lower phase is removed and the upper phase is concentrated under reduced pressure. A further 60 ml of ethyl acetate are then added and the solution is placed overnight in a freezer. A two-phase medium is obtained. The lower phase is removed and the upper phase is concentrated under reduced pressure. The yellow oil obtained is purified by chromatography on a column of silica gel with ethyl acetate as eluent, and then with a gradient of ethanol to give 3.6 g of diethyl 12-N-(aminoethyl)aminododecyl-phosphonate in a yield of 99%.

Characterization of diethyl 12-N-(aminoethyl)aminododecyl-phosphonate

Rf: 0.05 (EtOH Abs.)

$^1$H NMR (250 MHz, $CDCl_3$, ppm): 1.09-1.97 (m, 31H, $CH_3CH_2O$, NH, $NH_2$, $P(CH_2)_{11}$) 2.54-2.68 (m, 4H, $CH_2$—$NH_2$, $CH_2$—NH), 2.79 (t, 2H, $CH_2$—NH), 4.07 (m, 4H, $CH_2O$).

$^{13}$C NMR (100 MHz, $CDCl_3$, ppm): 16.9 (d, $OCH_2$), 22.8 (d, $CH_2$—$CH_2$—P), 24.7-27.4 (d, $CH_2$—P), 29.4-30.6 (m, $P(CH_2)_3$—$(CH_2)_8$)) 31.0 (d, $CH_2$—$(CH_2)_2$—P) 42.2 (s, $CH_2$—$NH_2$) 50.3 (s, $CH_2$—NH), 53 (s, HN—$CH_2$—$CH_2$—$NH_2$), 61.7 (d, $CH_2O$).

$^{31}$P NMR (101 MHz, $CDCl_3$, ppm): 33.9

Preparation of the Modified Titanium Sheet

A titanium sheet is modified with AEADPE under the same operating conditions as for Example 4, replacing the APPE solution with a solution of AEADPE in chloroform of concentration 1 mM.

This sheet is then placed for 3 days at 25° C. in a reactor under 5 bar of NO. The reactor is then purged with dry argon.

Example 7

Preparation of a Stainless-Steel Sheet Modified with MDPA and $Ag^+$ Ions

Preparation of MDPA

MDPA is prepared according to the procedure described in Example 1.

Preparation of the Modified Stainless-Steel Sheet

A sheet of stainless steel (supplied by Goodfellow, reference AISI 316) 0.15 mm thick, whose composition is as follows: 69% Fe, 18% Cr, 10% Ni, 3% Mo, is modified with MDPA under the same conditions as for the titanium sheet of Example 1.

This sheet is then immersed for 2 hours in 5 ml of a solution of $AgNO_3$ of concentration 1 mM in deionized water, and is then rinsed successively with water, with ethanol and with chloroform.

Example 8

Preparation of a Stainless-Steel Sheet Modified with AEPA and Nitrogen Monoxide

A stainless-steel sheet identical to that of Example 7 is modified with AEPA and nitrogen monoxide under the same operating conditions as for the titanium sheet described in Example 3.

Example 9

Preparation of a Stainless-Steel Sheet Modified with APPE and Nitrogen Monoxide

A stainless-steel sheet identical to that of Example 7 is modified with APPE and nitrogen monoxide under the same operating conditions as for the titanium sheet described in Example 4.

Example 10

Preparation of a Stainless-Steel Sheet Modified with MImBPPA

Preparation of $Br^-Me$—$C_3H_3N_2$—$(CH_2)_3$—$PO_3H_2$ (MImBPPA)

This compound is obtained in two steps. In the first step, MImBPPE is prepared according to the procedure described in Example 5.

In the second step, 7.15 g (6.31 mmol) of diethyl 3-(N-methylimidazolium bromide)propylphosphonate in 40 ml of dry $CH_2Cl_2$ are reacted, under an inert atmosphere, with 2.5 ml (18.93 mmol) of bromotrimethylsilane with stirring for 12 hours at room temperature. The solution obtained is then concentrated under reduced pressure, followed by addition of 40 ml of $CH_2Cl_2$ and 1.7 ml of distilled water. After stirring for 12 hours at room temperature and evaporating off the solvent, the oil obtained is washed with diethyl ether. After separation of the two phases, the oil is dissolved in distilled water and extracted with diethyl ether. The aqueous phase is then concentrated under reduced pressure to give 1.6 g of MImBPPA (89% yield).

Characterization of MImBPPA $^1$H NMR (δ, ppm, 200 MHz, D$_2$O): 1.6 (m, 2H, CH$_2$—CH$_2$—CH$_2$—P), 2.0 (m, 2H, CH$_2$—P), 3.7 (s, 3H, CH$_3$—N), 4.15 (t, 2H, CH$_2$—N), 7.3 (d, 2H, N—CH—CH—N), 8.6 (s, 1H, N—CH—N).

$^{31}$P NMR (δ, ppm, 81 MHz, D$_2$O): 30.35.

$^{13}$C NMR (δ, ppm, 100 MHz, D$_2$O): 23.3 ppm (CH$_2$—CH$_2$—P), 23.5 (d, CH$_2$—P), 36.2 (s, CH$_3$—N), 49.7 (d, CH$_2$—N), 123.5 (d, N—CH—CH—N), 136.4 (N—CH—N).

Preparation of a Stainless-Steel Sheet Modified with Br$^-$Me—C$_3$H$_3$N$_2^+$—(CH$_2$)$_3$—PO$_3$H$_2$ (MImBPPA)

A stainless-steel sheet identical to that of Example 7 is modified with MImBPPA under the same operating conditions as for the titanium sheet described in Example 1.

Example 11

Preparation of a Stainless-Steel Sheet Modified with MImBPPE

A stainless-steel sheet identical to that of Example 7 is modified with MImBPPE under the same operating conditions as for the titanium sheet described in Example 5. Analysis of the surface by SIMS (secondary ion mass spectrometry) confirms the grafting (presence of carbon and nitrogen).

Example 12

Preparation of a Stainless-Steel Sheet Modified with BDPA and then with Triethylamine Preparation of 12-Bromododecylphosphonic Acid (BDPA)

The compound BDPA was synthesized in two steps. In the first step, diethyl 12-bromododecylphosphonate is prepared as specified in Example 1. In the second step, diethyl 12-bromododecylphosphonate (2.43 g; 6.32 mmol) is reacted with Me$_3$SiBr (2.89 g; 18.93 mmol) in 50 ml of dry CH$_2$Cl$_2$ with stirring at room temperature for 12 hours.

After concentrating by evaporating under reduced pressure, 50 ml of dry CH$_2$Cl$_2$ and then 1.7 ml (0.095 mol) of water are added. The mixture obtained is stirred for 3 hours at room temperature and the solvent is then evaporated off and the BDPA is purified by recrystallization from dry CH$_2$Cl$_2$ (89% yield).

Characterization of BDPA $^1$H NMR (δ, ppm, 200 MHz, DMSO): 1.2-1.6 (m, 20H, CH$_2$), 1.79 (q, 2H, CH$_2$—CH$_2$—Br), 3.53 (t, 3H, 2H, CH$_2$—Br).

$^{31}$P NMR (δ, ppm, 81 MHz, DMSO): 27.87.

Preparation of a Stainless-Steel Sheet Modified with BDPA

A stainless-steel sheet identical to that of Example 7 is modified with BDPA under the same operating conditions as for the stainless-steel sheet described in Example 10.

Preparation of a Stainless-Steel Sheet Modified with BDPA and then with Et$_3$N

The stainless-steel sheet modified with BDPA is heated at 78° C. for 24 hours in a solution of 2 ml (14.4 mmol) of triethylamine in 11 ml of absolute ethanol. After cooling to room temperature, the stainless-steel sheet is washed with ethanol and then rinsed with water, with ethanol and with chloroform.

Example 13

Preparation of a TiO$_2$ Powder Modified with MImBPPE

Preparation of the Compound MImBPPE

The compound MImBPPE is prepared according to the procedure described in Example 5.

Preparation of the Modified TiO$_2$ Powder 150 ml of a solution of MImBPPE in chloroform, at a concentration of 1 mM, are added to 150 mg of TiO$_2$ (sold by the company Norpro, with a specific surface area of 120 m$^2$/g) in a 250 ml round-bottomed flask. The mixture is maintained at the reflux point of the chloroform for one week. After cooling to room temperature, the solution is removed by filtering through a Millipore sinter. The powder is then washed thoroughly with chloroform and then rinsed successively with water, ethanol, chloroform and acetone, and then dried under reduced pressure at 120° C. for 15 hours. Characterization of the powder by NMR of the solid confirms the grafting ($^{31}$P, ppm: 26.5; $^{13}$C, ppm: 138.6; 125.0; 59.4; 52.3; 38.4; 26.6; 18.3).

Example 14

Preparation of a TiO$_2$ Powder Modified with BDPA and then with Triethylamine

Preparation of 12-Bromododecylphosphonic Acid (BDPA)

The compound BDPA is prepared according to the procedure described in Example 12.

Preparation of the Modified TiO$_2$ Powder 200 ml of a solution of BDPA in absolute ethanol (concentration 1 mM) are added to 200 mg of TiO$_2$ (sold by Norpro) in a 250 ml round-bottomed flask. The mixture is stirred for three days at room temperature. After filtering and washing with ethanol, this powder is then heated at the reflux temperature of a mixture of triethylamine (2 ml) and ethanol (11 ml) for 24 hours. After cooling to room temperature, the powder is washed with ethanol and with acetone, and then dried under reduced pressure at 120° C. for 15 hours. Characterization of the powder by $^{31}$P NMR of the solid confirms the grafting (large peak centered at 26.3 ppm).

Example 15

Preparation of a TiO$_2$ Powder Modified with DMADPE and then with Ethyl Bromide Preparation of DMADPE DMADPE is prepared by reacting dimethylamine with diethyl bromododecylphosphonate (prepared according to the procedure described in Example 1).

2 g (5.19 mmol) of BDPE in 25 ml of acetonitrile are added dropwise to 0.24 g (5.19 mmol) of dimethylamine, 1.43 g (10.39 mmol) of K$_2$CO$_3$ and 75 ml of acetonitrile heated to 90° C. under an inert atmosphere. After 12 hours at 90° C., the reaction mixture is cooled to room temperature, the salts are removed by filtration and the filtrate is concentrated to give a yellow oil. This oil is purified on a column of silica gel (eluent: 85/15 to 70/30 EtOAc/MeOH) to give the DMADPE.

Characterization of DMADPE $^{31}$P NMR (CDCl$_3$): 33.19

$^1$H NMR (CDCl$_3$): 4.13 (m, O—CH$_2$, 4H); 2.62 (t, CH$_2$—N, 2H); 2.51 (s, 6H); 1.83-1.25 (broad peak, (CH$_2$)$_{11}$+OCH$_2$CH$_3$, 28H)

Preparation of the Modified TiO$_2$ Powder 150 ml of a solution of DMADPE in chloroform, at a concentration of 1 mM, are added to 150 mg of TiO$_2$ in a 250 ml round-bottomed flask. The mixture is maintained at the reflux temperature of the chloroform for one week. After filtering and washing with chloroform and then with ethanol, this powder is then heated at the reflux temperature of a mixture of bromoethane (5 ml) and ethanol (8 ml) for 24 hours. After cooling to room temperature, the solid is then washed and dried as in Example 13. Characterization of the powder by $^{31}$P NMR of the solid confirms the grafting (broad peak centered at 26.1 ppm).

Example 16

Preparation of a Hydroxyapatite Powder Modified with MImBPPE

Preparation of MImBPPE

MImBPPE is synthesized according to the procedure described in Example 5.

Preparation of the Modified Hydroxyapatite Powder 200 ml of a solution of MImBPPE in ethanol (concentration of 1 mM) are added to 360 mg of hydroxyapatite (sold by the company Acros, specific surface area 67 m$^2$/g) in a 250 ml round-bottomed flask.

The mixture is refluxed for 3 days. After cooling to room temperature, the solid is then washed and dried as in Example 13. Characterization of the powder by $^{31}$P NMR of the solid confirms the grafting (broad peak centered at 25.8 ppm in addition to a signal at 2.6 ppm derived from the phosphate units of hydroxyapatite).

Example 17

Preparation of a Calcium Carbonate Powder Modified with MImBPPE

Preparation of MImBPPE

MImBPPE is synthesized according to the procedure described in Example 5.

Preparation of the Modified Calcium Carbonate Powder 100 ml of a solution of MImBPPE in ethanol (concentration of 1 mM) are added to 400 mg of CaCO$_3$ (specific surface area 30 m$^3$/g) in a 250 ml round-bottomed flask. The mixture is stirred for 3 days at room temperature. The solid is then washed and dried as in Example 13. Characterization of the powder by $^{31}$P NMR of the solid confirms the grafting (broad peak centered at 26.3 ppm).

Example 18

Preparation of a Hydroxyapatite Powder Modified with BDPA and then with Triethylamine Preparation of 12-Bromododecylphosphonic Acid (BDPA)

The compound BDPA was synthesized according to the procedure described in Example 12.

Preparation of the Modified Hydroxyapatite Powder

A solution of 12-bromododecylphosphonic acid in absolute ethanol (1 mM) is adjusted to pH=6 by adding 0.1 M NaOH solution. 200 ml of this solution are added to 360 mg of hydroxyapatite (sold by the company Acros, specific surface area 67 m$^2$/g) in a 250 ml round-bottomed flask. The mixture is stirred for 3 days at room temperature.

After washing with ethanol, this powder is refluxed for hours in absolute ethanol, and is then heated at the reflux temperature of a mixture of triethylamine (2 ml) and ethanol (11 ml) for 24 hours. After cooling to room temperature, the solid is then washed and dried as in Example 13. Characterization of the powder by $^{31}$P NMR of the solid confirms the grafting (broad peak centered at 26.1 ppm).

Example 19

Preparation of a Calcium Carbonate Powder Modified with BDPA and then with Triethylamine Preparation de 12-Bromododecylphosphonic Acid (BDPA)

The compound BDPA was synthesized according to the procedure described in Example 12.

Preparation of the Modified Calcium Carbonate Powder

A solution of 12-bromododecylphosphonic acid in absolute ethanol (1 mM) is adjusted to pH=6 by adding 0.1 M NaOH solution. 100 ml of this solution are added to 400 mg of CaCO$_3$ (specific surface area 30 m$^2$/g) in a 250 ml round-bottomed flask. The mixture is stirred for 3 days at room temperature.

After washing with ethanol, this powder is refluxed for hours in absolute ethanol, and is then heated at the reflux temperature of a mixture of triethylamine (2 ml) and ethanol (11 ml) for 24 hours. After cooling to room temperature, the solid is then washed and dried as in Example 13. Characterization of the powder by $^{31}$P NMR of the solid confirms the grafting (broad peak centered at 26.5 ppm).

Example 20

Bacteriological Tests

The bacteriological tests were performed using the bacterium *Pseudomonas aeruginosa*.

These tests were performed on the samples obtained in Examples 1 to 4 and 6 to 12, referred to hereinbelow, respectively, as "samples H, A, B, I, M, C, D, E, O, N, P", and on 8 control samples.

The control samples are constituted of a titanium sheet (samples F and J), a stainless-steel sheet (samples G and Q), a titanium sheet modified with MDPA (sample K), a titanium sheet modified with APPE (sample L), a titanium sheet modified with AEADPE (sample R) and a stainless-steel sheet modified with BDPA (sample S). The sheets serving as control modified with MDPA, with APPE, with AEADPE and with BDPA were prepared under the same operating conditions as those described, respectively, in Examples 1, 4, 6 and 12. All the sheets serving as control were, before being used for the tests, immersed in 5 ml of absolute ethanol.

The samples (sheets of dimensions 1 cm×1 cm for samples A to G and sheets of dimensions 1.8 cm×1.8 cm for samples H to S) are placed vertically in the wells of a culture plate.

A culture medium for bacteria (of Muller Hinton type) is introduced, followed by a homogeneous suspension of bacteria (with an optical density at 600 nm equal to 0.05).

The culture plate is placed for 72 hours in an oven at 37° C. under CO$_2$ (humid atmosphere). A film of bacteria forms on the surface of the samples.

After washing with water to remove the non-adherent bacteria that do not form the biofilm, the samples are stained with crystal violet (which is a dye that selectively binds to bacteria) and then rinsed thoroughly with water to remove the excess crystal violet. 1 ml of DMSO is then added to dissolve the crystal violet. Measurement of the optical density at 600 nm of the solutions of dye in DMSO makes it possible to quantify the bacteria originating from the biofilm.

The results of the bacteriological tests are collated in the table below.

| Sample | Optical density at 600 nm normalized to 100% per unmodified support (Ti or steel) | Reduction relative to the unmodified support (Ti or steel) |
|---|---|---|
| A (Ti/MDPA/Ag⁺ ions) | 34.8 | −65% |
| B (Ti/AEPA/NO) | 20.5 | −80% |
| C (Steel/MDPA/Ag⁺ ions) | 17.2 | −83% |
| D (Steel/AEPA/NO) | 11.4 | −89% |
| E (Steel/APPE/NO) | 20.2 | −80% |
| F (Ti) | 100 | / |
| G (Steel) | 100 | / |
| H (Ti/MDPA/Ag nanoparticles) | 26.8 | −73% |
| I (Ti/APPE/NO) | 25.4 | −75% |
| J (Ti) | 100 | / |
| K (Ti/MDPA) | 90 | −10% |
| L (Ti/APPE) | 101 | +1% |
| M (Ti/AEADPE/NO) | 17.3 | −83% |
| N (Steel/MImBPPE) | 31.7 | −68% |
| O (Steel/MImBPPA) | 28.6 | −71% |
| P (Steel/BDPA/Et₃N) | 36.5 | −64% |
| Q (Steel) | 100 | / |
| R (Ti/AEADPE) | 86.4 | −14% |
| S (Steel/BDPA) | 96.8 | −3.2% |

For all the samples that release Ag⁺ ions or nitrogen monoxide (samples A, B, C, D, E, H, I and M), a very marked reduction (65% to 89%) in the number of adherent bacteria forming a biofilm is observed, relative to the control samples (unmodified Ti or steel supports). Furthermore, for samples K, L and R, before reaction with the Ag⁺ ions, the silver nanoparticles or NO, the reduction is much lower (<15%). This confirms that the antibacterial activity originates from the release into the physiological medium of the Ag⁺ ions or of the nitrogen monoxide present on the substrates modified via the process according to the invention.

For the samples with quaternary ammonium functions (samples N, O and P), the reduction in the number of adherent bacteria forming a biofilm, relative to the control samples (unmodified Ti or steel supports), is between 64% and 68%. The reduction is very low for sample S, modified solely with BDPA. The antibacterial activity thus indeed originates from the presence of the quaternary ammonium functions on the substrates modified via the process according to the invention.

The invention claimed is:

1. A process for preparing an antimicrobial inorganic substrate, said process comprising coupling a functional group with an antimicrobial property onto a surface of said substrate in one or more steps by means of an organophosphorus coupling agent, wherein:

the substrate is selected from the group consisting of metals, metal oxides, metal hydroxides, metal carbonates and metal phosphates;

the organophosphorus coupling agent is selected from the group consisting of phosphonic acids and phosphonates of formula $RPO(OX)_2$, bis-phosphonates of formula $RR'[PO(OX)_2]_2$, the phosphinic acids and phosphinates of formula $RR'PO(OX)$, monoalkyl phosphates of formula $ROPO(OX)_2$, and the dialkyl phosphates of formula $(RO)(R'O)PO(OX)$, in which:

X represents a hydrogen atom or a group selected from the group consisting of metal ions, ammonium ions, alkyl or aryl groups containing from 1 to 6 carbon atoms and trialkylsilyl groups containing from 1 to 6 carbon atoms;

R is an organic group selected from the group consisting of:

(a) a group that is capable of releasing antimicrobial nitrogen monoxide;

(b) a group which, after modification, has an intrinsic antimicrobial property or is capable of releasing species with antimicrobial properties, said group being selected from the group consisting of $-(CH_2)_n-SH$, $-(CH_2)_n-CN$, $-(CH_2)_n-NMe_2$, and $-(CH_2)_{n'}-Hal$, Hal representing a halogen atom n being between 1 and 20, n' being between 1 and 5 and n" being between 1 and 10; wherein the group is modified by immersion in a solution of silver nanoparticles or in a solution of $AgNO_3$; and (c) a group which is selected from $-(CH_2)_n-Br$ wherein by heating in a solution of trithylamine, n being between 1 and 20;

R' is a hydrogen atom, a hydroxyl group or an organic group corresponding to the definition given for the groups R; and the organophosphorus coupling agent is attached to the surface of the substrate via M—O—P bond in which M represents the metal of the substrate, said bond M—O—P being originated from condensation of P=OX and/or from coordination of phosphoryl groups.

2. The process as claimed in claim 1, wherein the group capable of releasing antimicrobial nitrogen monoxide is selected from the group consisting of diazenium diolate and oxynitroxy.

3. The process as claimed in claim 1, wherein the group R is selected from the group consisting of $-(CH_2)_n-NH_2$ and $-(CH_2)_n-NH-(CH_2)_2-NH_2$, and said group is modified by placing under an atmosphere of nitrogen monoxide gas.

4. The process as claimed in claim 1, wherein the coupling agent is selected from the group consisting of 12-mercaptododecylphosphonic acid (MDPA), 2-aminoethylphosphonic acid (AEPA), diethyl 3-aminopropylphosphonate (APPE), 12-bromododecylphosphonic acid (BDPA), diethyl 3-(N,N-dimethylamino)dodecylphosphonate (DMADPE), diethyl 3-(N-methylimidazolium bromide)propylphosphonate (MImBPPE), 3-(N-methylimidazolium bromide)propylphosphonic acid (MImBPPA) and diethyl 12-N-(aminoethyl)aminododecyl-phosphonate (AEADPE).

5. The process as claimed in claim 1, wherein the substrate to be treated is selected from the group consisting of a stainless steel, a galvanized steel, titanium, hydroxyapatite-coated titanium, a titanium-based or chromium-based alloy, aluminum, copper, titanium oxide, zirconium oxide, aluminum oxide, a calcium carbonate and hydroxyapatite.

6. The process as claimed in claim 1, wherein the coupling agent is grafted onto the surface of said substrate by immersing said substrate in a solution containing said coupling agent.

7. The process as claimed in claim 6, wherein the concentration of the coupling agent in the solution is between 0.1 and 100 mM.

* * * * *